United States Patent [19]

El-Rashidy

[11] Patent Number: 4,978,532
[45] Date of Patent: Dec. 18, 1990

[54] DOSAGE FORM FOR ADMINISTRATION OF DEHYDROEPIANDROSTERONE

[75] Inventor: Tahany El-Rashidy, Deerfield, Ill.

[73] Assignee: Pharmedic Co., Wheeling, Ill.

[21] Appl. No.: 392,728

[22] Filed: Aug. 11, 1989

[51] Int. Cl.⁵ .............................................. A61F 13/00
[52] U.S. Cl. ................................... 424/448; 424/449; 424/78; 424/486
[58] Field of Search ............... 424/448, 449, 443, 446, 424/78, 486; 514/866, 885, 909, 929

[56] References Cited

U.S. PATENT DOCUMENTS 4,727,064  2/1988  Pitha ....................................... 514/58
4,883,669  11/1989  Chien ................................... 424/448
4,895,727  1/1990  Allen .................................... 424/642

Primary Examiner—Merrell C. Cashion, Jr.
Assistant Examiner—Gabrielle Phelan
Attorney, Agent, or Firm—Dressler, Goldsmith, Shore, Sutker & Milnamow

[57] ABSTRACT

A dosage form for the delivery of dehydroepiandrosterone (DHEA) to a patient is described. The dosage form has an adhesive matrix containing a pressure-sensitive medical-grade silicone adhesive, DHEA, and a permeation enhancer for DHEA. The permeation enhancer is an aromatic or aliphatic carbocyclic compound with pendant hydroxyl groups.

13 Claims, 1 Drawing Sheet

Me = methyl ($CH_3$)
R = OH, $CH_3$, $O-Si(R)_3$ (i)

Me = methyl ($CH_3$)
R = $CH_3$, $O-Si(R)_3$ (ii)

DOSAGE FORM FOR ADMINISTRATION OF DEHYDROEPIANDROSTERONE

TECHNICAL FIELD

The present invention is directed to a drug delivery dosage form for transdermal administration of dehydroepiandrosterone to a patient. The dosage form also contains an adhesive matrix containing a pressure-sensitive silicone adhesive, and a permeation enhancer for dehydroepiandrosterone.

BACKGROUND OF THE INVENTION

Dehydroepiandrosterone (DHEA) is an abundantly produced adrenal steroid. The serum concentration of its sulfate ester (DHEA-S) is approximately 20 times higher than that of any other circulating steroid hormone. Nestler et al., J. Clin. Endocrinol. Metab. 66:57 (1988). Peak serum DHEA and DHEA-S levels occur in a human at or about the age of 25 years and decrease rapidly thereafter to only about 10 percent of peak level by the age of 80–90 years. Despite the abundance and rapid turnover of this hormone, the physiological role of DHEA is still relatively unknown.

In the adrenal cortex, under stimulation of adrenocorticotrophic hormone (ACTH), cholesterol is degraded to pregnenolone, oxidized to progesterone, and further converted to cortisol. It is not known whether DHEA synthesis follows the same biosynthesis route as cortisol. Although DHEA is produced by the adrenal cortex, it is not found in the adrenal gland. The above-described biosynthetic route is duplicated in the testes and ovaries, except that the final products are testosterone and estradiol, respectively. Each gland secretes its own hormone while de-emphasizing the other product. While DHEA is not stored in the gonads, its secretion into blood plasma is similar to that for the DHEA of adrenal origin. The plasma level of DHEA is not significantly affected by castration; however, it is almost completely obliterated by adrenalectomy.

In young humans, the total rate of secretion of DHEA is about 5–10 mg per day. This secretion comes mostly from the adrenal cortex with a small amount coming from the testes or ovaries. After sexual maturity, the level of secretion of DHEA diminishes and almost ceases at senescence. This is not true for other hormones such as cortisol, ACTH or testosterone which remain fairly constant with age. While ovarian estrogen secretions cease in females at menopause, considerable amounts of estrogens can continue to be produced via the liver and intestinal conversion of DHEA to estradiol.

Recent studies in animals demonstrate that DHEA has beneficial effects in obesity and breast cancer. Schwartz Cancer Res. 39:1129 (1979); Schwartz Nutrition and Cancer, 3:46 (1981). DHEA also has been shown to have antihypercholesterolic effects in lowering lipid levels in rats. Ben-David et al., Proc. Soc. Exp. Biol. Med., 125:1136 (1967).

The importance of hypercholesterolemia, an elevated low-density lipoprotein (LDL) cholesterol level, as a major risk factor for the development of ischemic heart disease is widely accepted.

Barrett-Connors et al., New Engl. J. Med. 315:1519 (1986) showed that individuals with low circulating levels of DHEA-S die of heart disease at a higher rate than normal subjects. The oral administration of DHEA (1600 mg/day) reduces total serum cholesterol and LDL level by about 7.1 and 7.5 percent, respectively, in normal subjects. However, the administration of such relatively high doses of DHEA is undesirable.

The use of DHEA and other 17-keto steroids as medication for the prophylaxis and therapy of a retrovirus infection or for complications arising therefrom, e.g., acquired immune deficiency syndrome (AIDS) has been reported in SCRIP No. 1422, June 21, 1989, page 21 and in British Pat. Publication No. 2,204,237 by Colthurst, Ltd. Oral administration of relatively large doses of 1 to 2 grams per day has been tested in AIDS patients for improving their immune systems. In such tests, DHEA was administered orally alone or in combination with immunomodulators or antiviral agents.

Transdermal drug delivery devices for the continuous controlled transdermal administration of drugs are well known. Examples of such devices can be found in U.S. Pat. No. 3,731,683 to Zaffaroni, U.S. Pat. No. 3,797,494 to Zaffaroni, U.S. Pat. No. 4,031,894 to Uhrquhart et al., and U.S. Pat. No. 4,336,243 to Sanvordeker et al. Transdermal drug delivery devices are typically held in contact with the skin by means of a pressure-sensitive adhesive layer and are left in place for a period of 24 hours or longer.

Silicone pressure-sensitive adhesives are effective for holding such transdermal drug delivery systems to the skin for prolonged periods of time. Such silicone pressure-sensitive adhesives are known to be non-irritating and nonsensitizing to the skin, and have been used for the controlled release of nitroglycerin (Nitro-Disc ®, G.D. Searle Co., Skokie, Ill.). Other transdermal drug delivery systems have been developed for the delivery of various drugs. For example, the Transderm Scop ® system for the delivery of scopolamine (CIBA-Geigy, Ardsley, N.Y.) utilizes a polyisobutylene pressure-sensitive adhesive layer.

It has now been found that therapeutically effective amounts of DHEA can be administered transdermally from a silicone based pressure-sensitive adhesive matrix which maintains its tack and adherence throughout the administration of DHEA.

SUMMARY OF THE INVENTION

The present invention contemplates a drug delivery dosage form for the administration of dehydroepiandrosterone (DHEA) in a therapeutically effective amount to a human patient.

The dosage form of the present invention utilizes a pressure-sensitive medical grade silicone adhesive matrix which contains DHEA and a permeation enhancer therefor.

The contemplated permeation enhancer is an aromatic or aliphatic carbocyclic compound containing pendant hydroxyl groups, such as butylated hydroxytoluene (BHT), butylated hydroxyanisole (BHA) or a hydroxypropyl-beta-cyclodextrin (HPBCD), and the like, which is present in an amount up to about 30 percent by weight of the adhesive matrix.

The DHEA is present in the dosage form of the present invention in an amount in the range of about 1 to about 30 percent by weight of the adhesive matrix.

A preferred transdermal patch embodying the present invention includes an occlusive backing for the adhesive matrix.

DESCRIPTION OF PREFERRED EMBODIMENTS

Figure 1:
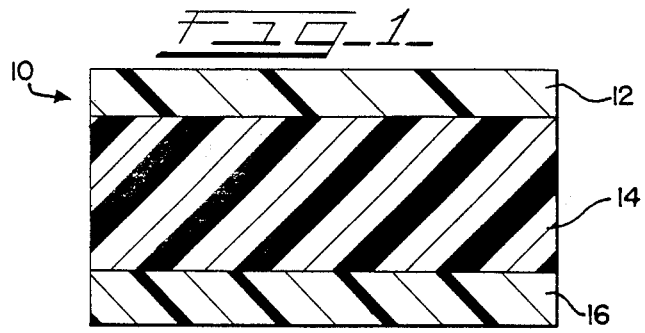
FIG. 1 shows a sectional elevation of a transdermal patch embodying the present invention.

The present invention provides an effective means for the delivery of DHEA to a patient over an extended time period from an adhesive matrix.

Dehydroepiandrosterone (DHEA) is a C-19 steroid as represented by Formula I.

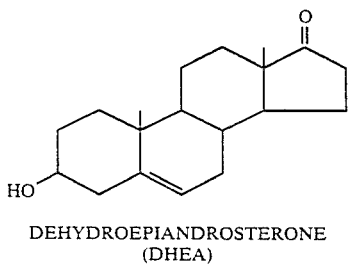

DEHYDROEPIANDROSTERONE
(DHEA)

DHEA is produced, inter alia, in the adrenal cortex of a mammal, and secreted principally as the sulfate salt. DHEA is a very weak androgen and little of it is utilized in vivo as a precursor for testosterone biosynthesis. However, elevated DHEA levels in vivo have been demonstrated to produce a reduction of cardiovascular risk factors in humans. Barrett-Connors et al., New Engl. J. Med. 315:1519 (1986).

The "therapeutically effective amount" to be delivered to a particular patient depends upon the patient's age, weight of the patient, the particular condition to be treated, and the like considerations. DHEA in the presently contemplated dosage forms can be administered to lower elevated blood cholesterol levels, for prophylactic or palliative treatment of patients suffering from AIDS, heart disease, obesity, diabetes, and the like afflictions.

A "permeation enhancer" as used herein is a compound compatible with DHEA that facilitates the uptake of DHEA through the skin and thus enables a therapeutically effective dosage of DHEA to be administered to the patient.

The presently contemplated permeation enhancers are aromatic or aliphatic carbocyclic compounds that have pendant hydroxyl groups, such as butylated hydroxytoluene (BHT), butylated hydroxyanisole (BHA), a hydroxypropyl-beta-cyclodextrin (HPBCD), and the like, as well as mixtures thereof.

The permeation enhancers of the present invention increase the permeability of the treated area of skin to DHEA to a magnitude such that sufficient DHEA is absorbed to provide a therapeutically effective, e.g., cholesterol-lowering level of DHEA in the bloodstream. The rate of permeation enhancer administration is controlled by its rate of release from the adhesive matrix to the skin surface. Thus the rate of DHEA administration is correlated with the concurrent rate of release of the permeation enhancer, since the permeation enhancer modulates the rate at which the skin absorbs the DHEA.

Preferred permeation enhancers are BHT, BHA and HPBCD, represented by Formulas II, III and IV, respectively:

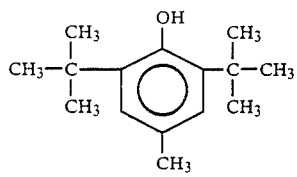

II

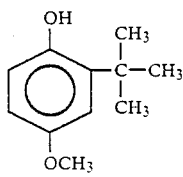

III

-continued

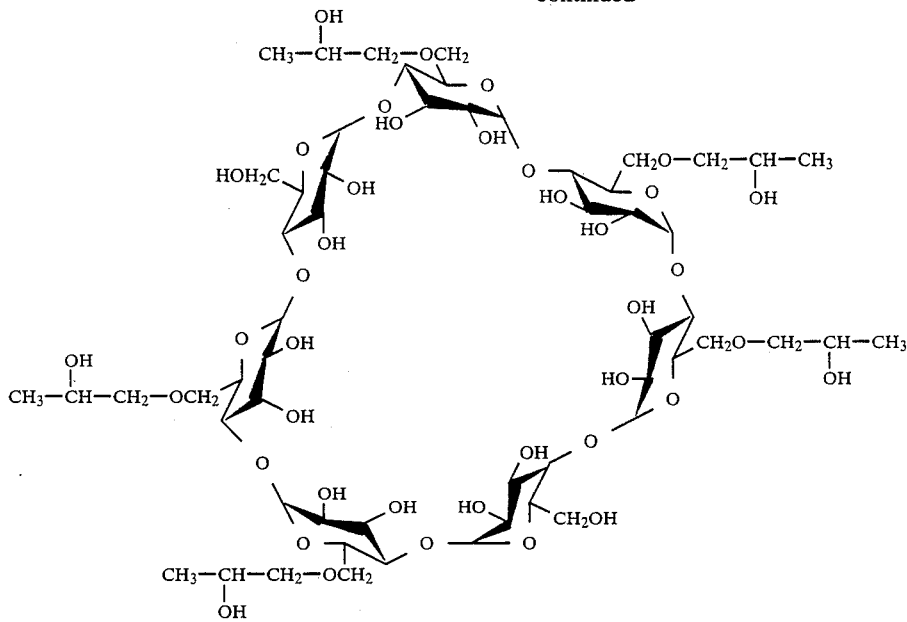

IV

BHT and BHA are commercially available compounds that are insoluble in water but soluble in organic solvents.

Hydroxypropyl-beta cyclodextrins are commercially available compounds that are derived from beta-cyclodextrins by condensation with a propylene oxide to provide the corresponding hydroxypropyl derivatives having a degree of substitution (D.S.) up to about 15 or higher. For the purposes of the present invention a D.S. value of about 5 to 7 is preferred.

The preparation of suitable hydroxypropyl-beta-cyclodextrins is described, inter alia, in International Journal of Pharmaceutics 29:73–82 (1986) and in Journal of Pharmaceutical Sciences 75 (6):571–572 (1986). Also known, and contemplated for the purposes of the present invention are the hydroxypropyl-beta-cyclodextrins that are polyethers of cyclodextrins and are obtained by condensation of an excess of hydroxypropylene oxide with beta-cyclodextrin as described in U.S. Pat. No. 3,459,731 to Gzamera et al.

In a preferred embodiment, a permeation enhancer in a transdermal patch of the present invention increases the rate of DHEA permeability into skin to a rate that is at least comparable to the rate of release of DHEA from the adhesive matrix.

The contemplated dosage form of the present invention is a transdermal patch in which the pressure-sensitive adhesive matrix provides contact with the skin surface of a patient and acts as reservoir for DHEA, permitting the DHEA present to permeate into the skin of the mammal at a therapeutically effective rate. The amount of DHEA present is in the range of about 1.0 to about 30 weight percent, preferably about 10 to about 25 weight percent, based on the weight of the adhesive matrix.

The concentration of the permeation enhancer varies dependent on the specific permeation enhancer utilized. In one embodiment, when the permeation enhancer is BHT, it is present in an amount in the range of about 0.1 to about 5 percent by weight of the adhesive matrix, preferably about 0.5 to about 1.0 percent by weight of the adhesive matrix. When a hydroxypropyl-beta-cyclodextrin is used as the permeation enhancer, it is present in an amount in the range of about 1 to about 20 percent by weight of the adhesive matrix, and preferably about 1 to about 10 percent by weight of the adhesive matrix. The weight ratio of DHEA-to-BHT is in the range of about 20 to about 1, preferably about 10 to about 1, and the weight ratio of DHEA-to-HPBCD is in the range of about 20 to about 1.

FIG. 1 illustrates a preferred discoid dosage form 10 in which a pressure-sensitive silicone adhesive matrix 14 containing DHEA and a permeation enhancer therefore is sandwiched between an occlusive backing 12 and a release liner 16. Occlusive backing 12 is a film usually having a thickness of about 2.5 to about 3 mils. Release liner 16 likewise has a usual thickness of about 2.5 to about 3 mils. The thickness of adhesive matrix 14 usually is about 10 mils. Removal of release liner 16 typically exposes a pressure-sensitive adhesive matrix surface of about 7 cm$^2$ across which a flux of DHEA is delivered to a patient when the exposed adhesive surface is placed in intimate contact with the patient's skin.

The adhesive matrix preferably is constituted by a medical grade pressure-sensitive silicone adhesive of the type shown in FIG. 2, such as BIO-PSA ® Q7-2920 [Structure (ii) when y is 500 to 1000], commercially available from Dow Corning Corporation, Midland, Mich. 48640, in a cyclohexane medium, and an aromatic or aliphatic carbocyclic permeation enhancer for DHEA, as described hereinabove.

Figure 3:
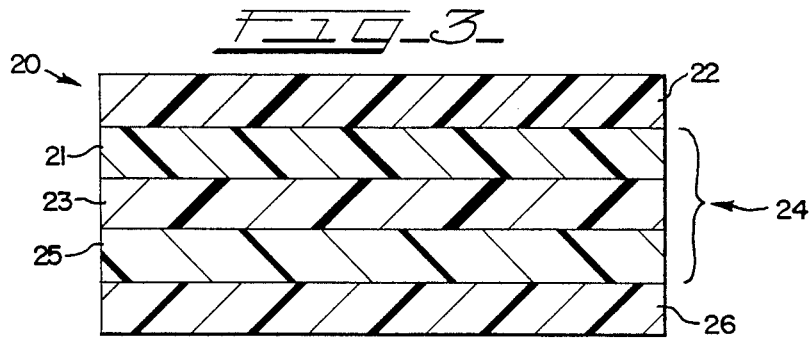
FIG. 3 shows a sectional elevation of a multilayered transdermal patch embodying the present invention.

In another embodiment, a dosage form of the present invention is a multilayered discoid patch in which the concentration of DHEA and permeation enhancer in the adhesive matrix varies in adjacent layers. FIG. 3 illustrates an exemplary multilayered dosage (20) form of the present invention in which a pressure-sensitive adhesive matrix 24 composed of three independent layers 21, 23 and 25, respectively, containing DHEA and a permeation enhancer therefore is sandwiched between an occlusive backing 22 and a release liner 26. The occlusive backing 22 and release liner 26 are as described for FIG. 1, hereinabove. The thickness of the adhesive matrix 24 is about 10 to about 20 mils. In a preferred embodiment a dosage form of the present invention has a skin contact adhesive layer containing a relatively high concentration of a permeation enhancer such as BHT and a relatively low concentration of DHEA. Successive additional adhesive layers are placed upon the preceding layer, where each successive layer has a relatively lower concentration of permeation enhancer and a relatively higher concentration of DHEA present in the adhesive matrix. An occlusive backing layer is present as the top, or skin-opposed, layer of the dosage form.

Several variations of the transdermal dosage form of the present invention are contemplated.

Illustrative dosage forms of the present invention include those in which the adhesive matrix between the occlusive backing film (BF) and the release liner on the skin contact surface (RL) is composed of a plurality of individual layers containing, in addition to the silicone pressure-sensitive adhesive, differing concentrations of permeation enhancer (PE) and/or DHEA sufficient to form a step-gradient of the respective components in the dosage form. Exemplary dosage forms include the following, where the virgule (/) represents the interface between individual layers and a series of three dots ( . . . ) indicates a plurality of intermediate layers of either successively increasing or successively decreasing concentrations of the active component(s) present in the adhesive matrix. In other words, the amount of DHEA and permeation enhancers is different in each layer. Additionally, a matrix can be present that contains neither DHEA nor a permeation enhancer therefor. Listed below, schematically, as progressing from a relatively "Higher" to a relatively "Lower" concentration, or vice versa, are the following illustrative dosage forms:

(a) [RL]/[Higher PE only]/[PE & Lower DHEA] . . . [PE & Higher DHEA]/[BF];

(b) [RL]/[PE & Lower DHEA] . . . [PE & Higher DHEA]/[BF];

(c) [RL]/[Higher PE] . . . [Lower PE only]/[matrix only]/[Lower DHEA only] . . . [Highest DHEA]/[BF]; and (d) [RL]/[Higher PE & DHEA] . . . [Lower PE & DHEA]/[matrix only]/Lower DHEA only] . . . [Higher DHEA]/[BF].

A dosage form, as described above, is also contemplated that contains different permeation enhancers in contiguous independent layers of the adhesive matrix. In one embodiment, a transdermal patch is contemplated containing an occlusive backing layer coextensive with a two-layer adhesive matrix. In this embodiment, the adhesive matrix is composed of a first layer coextensive with the backing layer and containing DHEA and a HPBCD together with the silicone adhesive, and a second layer contiguous with the first layer and containing DHEA and BHT together with the silicone adhesive. In a second embodiment a transdermal patch having a three-layer adhesive matrix contiguous to an occlusive backing layer is contemplated in which each layer of the matrix is composed of a silicone adhesive and, in addition, the first layer contains DHEA and a HPBCD, the second layer contains DHEA and BHT, and the third layer contains BHT alone.

Silicone pressure-sensitive adhesive compositions preferred for use in practicing the present invention are described in U.S. Pat. Nos. 4,591,622 to Blizzard et al.; 4,584,355 to Blizzard et al.; 4,585,836 to Homan et al.; and 4,655,767 to Woodard et al. The disclosures of the foregoing patents are incorporated herein by reference to the extent pertinent. Illustrative pressure sensitive silicone adhesives suitable for use in a transdermal drug delivery system are those described in Pfister, W. R., Pharmaceutical Technol. 13:126–138 (1989), whose disclosure is incorporated herein by reference.

An illustrative silicone pressure-sensitive composition is prepared as described hereinafter. About 40 to about 70 parts by weight of at least one benzene soluble resin copolymer containing silicon-bonded hydroxyl radicals and consisting essentially of $R_3SiO_{\frac{1}{2}}$ units and $SiO_{4/2}$ units in a mole ratio of 0.6 to 0.9 $R_3SiO_{\frac{1}{2}}$ units for each $SiO_{4/2}$ unit present (Component A), about 30 to about 60 parts by weight of at least one polydiorganosiloxane consisting essentially of ARSiO units terminated with endblocking $TRASiO_{\frac{1}{2}}$ units, each said polydiorganosiloxane having a viscosity of from 100 centipoise to 30,000,000 centipoise at 25 degrees C. where each T is R— or X— (Component B), a sufficient amount of at least one organosilicone endblocking agent capable of generating an endblocking triorganosilyl unit selected from the group consisting of $ZR_2Si$- units, $CH_3Z'$— units and $RZ''$— units and $Z'''R_2Si$— units to provide a 1:0.8 to 1:3 mole ratio of total silicon-bonded hydroxyl and X radicals present in Components A and B to total endblocking triorganosilyl units provided by all endblocking agent present, said agent being selected from the group consisting of $ZR_2SiY$, $(ZR_2Si)_qD$, $CH_3Z'Y$, $(CH_3Z')_2O$, $RZ''Y'$, $(RZ'')_2O$ and $Z'''R_2SiY'$ (Component C), an additional catalytic amount of a mild silanol condensation catalyst (Component D) in the event that none is provided by Component C, are admixed together with an organic solvent which is inert with respect to Components A, B, C, and D in an amount sufficient to reduce the viscosity of the resulting admixture, and this admixture is condensed at least until a substantial amount of the endblocking triorganosilyl units have reacted with the silicon-bonded hydroxyl radicals and X radicals of Components A and B.

In the aforementioned components, each R is a nonvalent organic radical selected from the group consisting of hydrocarbon radicals of from 1 to 6 inclusive carbon atoms, each X radical is selected from the group consisting of HO—, H—and R'O— radicals, each R' is an alkyl radical of from 1 to 4 inclusive carbon atoms, each Y radical is a monovalent hydrolyzable organic radical or HO—, each Y' is HO— or a monovalent hydrolyzable organic radical free of nitrogen, each A radical is selected from the group consisting of R— and halohydrocarbon radicals of from 1 to 6 inclusive carbon atoms such as chloromethyl, chloropropyl, 1-chloro-2-methylpropyl, 3,3,3-trifluoropropyl and $F_3C(CH_2)_5$— each Z radical is A— or QR"—, each R" is a divalent alkylene radical of from 1 to 6 inclusive carbon atoms, each Q is an organofunctional monovalent radical selected from the group consisting of RCO-E'—, RE'OC—, NC—, R'E'—, HO—, $G_2N$—, HO(R-"O)$_n$—, and $G_2NCH_2CH_2NG$— where E' is —O—, —NG—or —S—, n has a value of from 1 to 6,

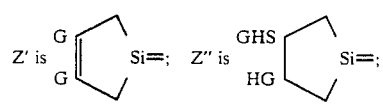

$Z'''$ is selected from the group consisting of HSR"—, $HSCH_2CH_2NGR''$— and $HOCH_2CH_2SR''$— radicals, each G is R'— or H—, D is a divalent or trivalent organic radical capable of being hydrolyzed to release said endblocking silyl units and q has a value of 2 when D is a divalent radical and q has a value of 3 when D is a trivalent radical.

Exemplary R groups include methyl, ethyl, propyl, isopropyl, hexyl, cyclohexyl, vinyl, allyl, propenyl and phenyl. Preferably, the $R_3SiO_{\frac{1}{2}}$ units are $Me_2R'''SiO_{\frac{1}{2}}$ units wherein R''' is a methyl ("Me"), vinyl ("Vi") or phenyl ("Ph") radical. More preferably, no more than 10 mole percent of the $R_3SiO_{\frac{1}{2}}$ units present in Component A are $Me_2R''''SiO_{\frac{1}{2}}$ units and the remaining units are $Me_3SiO_{\frac{1}{2}}$ units where each R'''' is a methyl or a vinyl radical.

More preferred are compositions employing about 50 to about 65 parts by weight of Component A and about 35 to about 50 parts by weight of Component B. For low tack adhesives, compositions having about 58 to about 65 parts by weight of Component A and about 35 to about 42 parts by weight of Component B are utilized.

The benzene-soluble silicone resin copolymers that constitute Component A are well-known materials. They contain silicon-bonded hydroxyl radicals in amounts which typically range from about 1 to 4 weight percent of silicon-bonded hydroxyl radicals and consist essentially of triorganosiloxy units of the formula $R_3SiO_{\frac{1}{2}}$ and tetrafunctional siloxy units of the formula $SiO_{4/2}$ in a mole ratio of from 0.6 to 0.9 $R_3Si_{\frac{1}{2}}$ units for each $SiO_{4/2}$ unit present. Blends of two or more such copolymers may also be used. There should be at least some and preferably at least 0.5% silicon-bonded hydroxyl content to enable the polydiorganosiloxane component to copolymerize with the copolymer resin and/or to react with the endblocking agent being added to chemically treat the silicone pressure-sensitive adhesive composition. These resin copolymers are benzene-soluble resinous materials which are typically solids at room temperature and are prepared as, and usually, but not necessarily used as, a solution in an organic solvent. Typical organic solvents used to dissolve Component A include benzene, toluene, xylene, methylene chloride, perchloroethylene, naphtha mineral spirits and mixtures of these.

A few mole percent of $R_2SiO$ units can be present in Component A if the presence of such units does not cause the ultimate product to lose its ability to function as a pressure-sensitive adhesive.

The mole ratio of $R_3SiO_{\frac{1}{2}}$ and $SiO_{4/2}$ units can be determined simply from a knowledge of the identity of the R radicals in the $R_3SiO_{\frac{1}{2}}$ units and the present carbon analysis of the resin copolymer. In the preferred-resin copolymer having from about 0.6 to about 0.9 $Me_3SiO_{\frac{1}{2}}$ units for every $SiO_{4/2}$ unit, the carbon analysis has a value of from about 19.8 to about 24.4 percent by weight.

Component A may be prepared according to U.S. Pat. No. 2,676,182 to Daudt et al. (hereby incorporated by reference) whereby a silica hydrosol is treated at a low pH with a source of $R_3SiO_{\frac{1}{2}}$ units such as a hexaorganodisiloxane such as $Me_3SiOSiMe_3$, $ViMe_2Si$-$OSiMe_2Vi$ or $MeViPhSiOSiPhViMe$ or triorganosilane such as $Me_3SiCl$, $Me_2SiCl$ or $MeViPhSiCl$. Such copolymer resins are typically made such that the copolymer resin contains about 1 to about 4 weight percent of silicon-bonded hydroxyl radicals. Component B is also a well-known material and is one or more polydiorganosiloxanes containing ARSiO units terminated with endblocking $TRASiO_{\frac{1}{2}}$ units, each of which polydiorganosiloxanes has a viscosity of from about 100 centipoise to about 30,000,000 centipoise at 25 degrees C. (about 100 millipascal seconds to about 30,000 pascal seconds (Pa.s) where 1 centipoise equals 1 millipascal second). As is well-known, viscosity is directly related to the average number of diorganosiloxane units present for a series of polydiorganosiloxanes of varying molecular weights which have the same endblocking units. Polydiorganosiloxanes having a viscosity of from about 100 to 100,000 centipoise at 25 degrees C. range from fluids to somewhat viscous polymers. These polydiorganosiloxanes are preferably prereacted with Component A prior to condensation in the presence of Component C to improve the tack and adhesion properties of the resulting pressure-sensitive adhesive as will be further described. Polydiorganosiloxanes having viscosities in excess of 100,000 centipoise can typically be subjected to the condensation and endblocking as described above. Polydiorganosiloxanes having viscosities in excess of 1,000,000 centipoise are highly viscous products often referred to as gums and the viscosity is often expressed in terms of a Williams Plasticity value (polydimethylsiloxane gums of about 10,000,000 centipoise viscosity typically have a Williams Plasticity value of about 50 mils (1.27 mm) or more at 25 degrees C).

Component B contains ARSiO units where each R and A, respectively are as defined above. Thus the polydiorganosiloxane can contain $Me_2SiO$ units, $PhMeSiO$ units, $MeViSiO$ units, $Ph_2SiO$ units, methylethylsiloxy units, 3,3,3-trifluoropropyl units and 1-chloro-2-methylpropyl units and the like. Preferably, the ARSiO units are selected from the group consisting of $R_2'''SiO$ units, $Ph_2SiO$ units and combinations of both where R''' is as above. At least 50 mole percent of the R''' radicals present in Component B are methyl radicals and no more than about 50 mole percent of the total moles of ARSiO units present in Component B are $Ph_2SiO$ units. More preferably, no more than 10 mole percent of the ARSiO units present in Component B are $MeR''''SiO$ units where R'''' is as above defined and the remaining ARSiO units present in each polydiorganosiloxane are $Me_2SiO$ units.

Each polydiorganosiloxane of Component B is terminated with endblocking units of the unit formula $TRASiO_{\frac{1}{2}}$ where R and A are as defined above and each T radical is R or X wherein each X radical is selected from HO—, H— and R'O— radicals, where each R' is an alkyl radical of from 1 to 4 inclusive carbon atoms such as methyl, ethyl, n-propyl, and isobutyl radicals. The X radicals provide a site for reaction with the endblocking triorganosilyl units of Component C and also provide a site for condensation with other X radicals on Component B or with the silicon-bonded hydroxyl groups present in Component A. Use of polydiorganosiloxanes where T is HO— is most preferred because the polydiorganosiloxane of Component B can then readily copolymerize with the resin copolymer Component A. When appropriate catalysts such as HCl or ammonia are used as endblocking agents, triorganosiloxy (e.g., $R_3SiO_{\frac{1}{2}}$ such as $(CH_3)_3SiO_{\frac{1}{2}}$ or $CH_2=CH(CH_3)_2SiO_{\frac{1}{2}}$) unit terminated polydiorganosiloxanes can be employed because some of the triorganosiloxy units can be cleaved when the condensation reaction is conducted with heating. The cleavage exposes a silicon-bonded hydroxyl radical which can then condense with silicon-bonded hydroxyl radicals in the copolymer resin, with endblocking triorganosilyl units or with other polydiorganosiloxanes containing X radicals or silicon-bonded hydroxyl radicals exposed by cleavage reactions. Mixtures of polydiorganosiloxanes containing different substituent radicals may also be used.

Methods for the manufacture of such polydiorganosiloxanes are well known as exemplified by U.S. Pat. Nos. 2,490,357 to Hyde; 2,542,334 to Hyde; 2,927,907 to Polmanteer; 3,002,951 to Johannson; 3,161,614 to Brown, et al.; 3,186,967 to Nitzche, et al.; 3,509,191 to Atwell and 3,697,473 to Polmanteer, et al. which are hereby incorporated by reference.

One embodiment of the dosage form of the present invention is a transdermal patch that contains an occlusive backing layer attached to the adhesive matrix on a face opposed to the surface capable of adhesively contacting a skin surface, and a release liner attached to the skin contact surface of the adhesive matrix.

Figure 2:
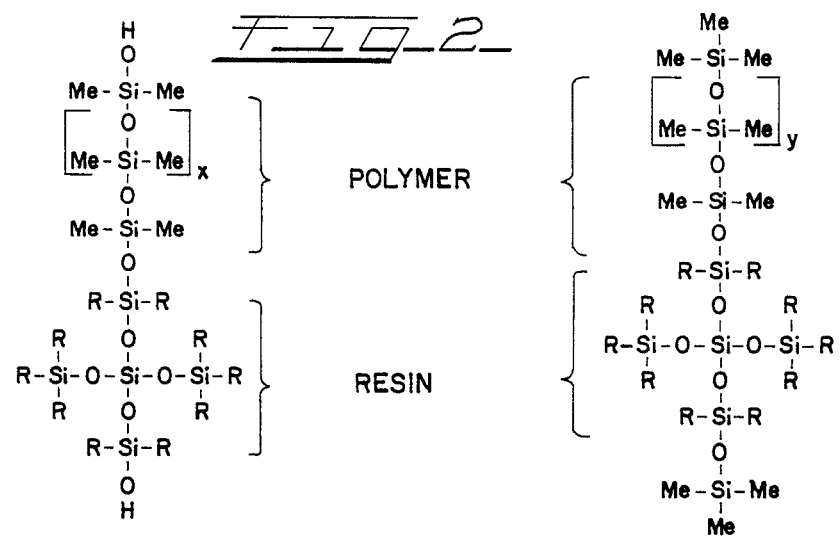
FIG. 2 shows the structures for two pressure-sensitive dimethyl silicone adhesives which are effective in the present invention. Replacement of the hydroxyl groups in Structure (i) with trimethyl siloxyl groups produce an amine-resistant silicone adhesive shown as Structure (ii). Values for x and y are in the range of about 500 to about 1000.

The adhesive matrix in this particular embodiment contains the pressure-sensitive medical-grade silicon adhesive, shown in FIG. 2 as Structure (ii), a permeation enhancer and DHEA. The adhesive matrix can contain a plurality of layers where each successive layer contains in addition to the adhesive varying concentrations of DHEA and/or a permeation enhancer. The occlusive backing layer is a polyester film [SCOTCHPAK ® 1006 Film (3M Co., St. Paul, Minn.)]. The release liner is another polyester film [SCOTCHPAK ® 1022 Film (3M Co., St. Paul, Minn.)], provided with a release surface.

In a particularly preferred embodiment, the transdermal patch has an adhesive matrix containing butylated hydroxytoluene (BHT) and DHEA, attached to an occlusive SCOTCHPAK ® 1006 Film backing layer. The transdermal patch is attached to the skin of a patient by contacting the skin with the adhesive.

The transdermal patch of the present invention is useful in the treatment of hypercholesterolemia and in the maintenance of lower blood cholesterol levels in a patient.

The continuous administration of DHEA to a patient produces a substantial cholesterol lowering effect. Application of the transdermal patch of the present invention to the skin of a patient allows a predetermined amount of DHEA to be administered continuously to the patient and thus avoids the undesirable effects present with single or multiple administration of larger DHEA dosages. By maintaining a sustained dosage rate, the DHEA level in the patient's blood can be continuously maintained within the optimal therapeutic range.

The present invention is further illustrated by the following EXAMPLES.

EXAMPLE 1: Transdermal Patches Without Enhancers

Transdermal patches (3 cm and 5 cm in diameter) were prepared for the delivery of DHEA. The patches were composed of a trilaminate of an adhesive matrix sandwiched between an occlusive backing layer and a release liner.

The adhesive matrix was prepared from the pressure-sensitive silicone adhesive composition BIOPSA ® Q7-2920 (obtained from Dow Corning Corp., Midland, Mich. 48686)in cyclohexane (50% w/v) together with DHEA (at concentrations of 0, 1, 5, 10 and 20 weight %).

The occlusive backing film was a SCOTCHPAK ® 1006 (3M Co., St. Paul, Minn.) polyester film (about 2.8 mil in thickness). The release liner was a polyester film (about 2.9 mil in thickness) of SCOTCHPAK ® 1022 (3M Co., St. Paul, Minn.).

The final transdermal patches were about 16 mil thick, 3 or 5 cm in diameter and had a surface area of about 7.1 $cm^2$ or 9.6 $cm^2$.

In use, the transdermal patch is applied to a patient by removing the release liner and contacting the adhesive unit with the skin of the patient.

EXAMPLE 2: Effect of DHEA and Permeation Enhancer Content Upon Properties of Transdermal Patches Patches were prepared as described in EXAMPLE 1. Transdermal patches containing 0, 1, 5, 10 or 20 weight % DHEA were evaluated in vitro. The performance of the patches with regard to (1) the removal of the release liner (Release), (2) adhesion to artificial surface, (Adhesion), and (3) tack (Tack) were then evaluated. The results are illustrated in TABLE I, below, where the ratings for Release, Adhesion and Tack are indicated as follows:

| Release | Adhesion | Tack |
|---|---|---|
| 1 = Very easy | 1 = Very good | 1 = Very sticky |
| 2 = Easy | 2 = Good | 2 = Sticky |
| 3 = Moderate | 3 = Fair | 3 = Fair |
| 4 = Difficult | 4 = Poor | 4 = Not much |
| 5 = No release | 5 = None | 5 = None |

TABLE 1

| Patch Diameter cm | Surface Area $cm^2$ | Adhesive mg | Permeation Enhancer Name Wt. % (mg) | DHEA Wt. % (mg) | Properties | | |
|---|---|---|---|---|---|---|---|
| | | | | | Release | Adhesion | Tack |
| 5 | 19.6 | 680.4 ± 75.0 | — | 0(0) | 1 | 2 | 3 |
| 5 | 19.6 | 692.1 ± 52.1 | — | 10(69.3 ± 5.2) | 1 | 2 | 3 |
| 5 | 19.6 | 695.3 ± 40.0 | — | 5(33.0 ± 2.0) | 1 | 2 | 4 |
| 5 | 19.6 | 723.9 ± 47.8 | — | 1(7.2 ± 0.5) | 1 | 2 | 4 |
| 3 | 7.1 | 184.6 ± 16.2 | — | 0(0) | 1 | 2 | 3 |
| 3 | 7.1 | 216.8 ± 20.6 | — | 10(21.7 ± 2.06) | 1 | 2 | 3 |
| 3 | 7.1 | 208.3 ± 31.9 | — | 5(10.4 ± 1.6) | 1 | 2 | 3 |
| 3 | 7.1 | 231.5 ± 21.6 | — | 1(2.3 ± 0.2) | 1 | 2 | 3 |
| 3 | 7.1 | 256 ± 36 | — | 0(0) | 1 | 1 | 3 |
| 3 | 7.1 | 266 ± 9 | — | 10(26.6 ± 0.9) | 1 | 1 | 3 |
| 3 | 7.1 | 277 ± 11 | BHT 0.5 (1.4 ± .1) | 10(27.7 ± 1.0) | 1 | 1 | 2 |
| 3 | 7.1 | 271 ± 10 | BHT 1.0 (2.8 ± .1) | 10(27.4 ± 1.0) | 2 | 1 | 2 |
| 3 | 7.1 | 265 ± 5 | HPBCD 1.0 (2.7 ± .1) | 10(26.5 ± 0.5) | 1 | 1 | 2 |
| 3 | 7.1 | 306 ± 20 | HPBCD 5.0 (15.3 ± 1) | 10(30.6 ± 2.0) | 1 | 1 | 3 |

EXAMPLE 3: Transdermal Patch Performance on Human Subject

Transdermal patches were prepared as described in EXAMPLE 1 containing 0, 5 or 10 weight percent DHEA. The patches were adhered to the skin of a 42 years old male for 3 days of continuous wear. During this three-day period, the subject reported mild headaches while the patches were worn, which is indicative of DHEA absorption through the skin at a level sufficient to elicit a biologic response. No skin irritation or sensitization was reported. The patches remained adhered to the skin during repeated bathing and showers and were easily removed after the three-day period.

EXAMPLE 4: Preparation of DHEA-Containing Transdermal Patches With Enhancers

A solution of BIO-PSA ® Q7-2920 (50 weight percent in hexane) obtained from Dow Corning Corp., Midland, Mich. 48686 was filtered through 16-ply Dacron ® mesh to remove any particles present from the solution.

Aliquots of the filtered solution (100 gm each) were then mixed with sufficient DHEA to produce individual solutions containing 0, 1, 5 and 10 weight percent, respectively, of DHEA.

Individual solutions were then mixed with sufficient amounts of a hydroxypropyl-beta-cyclodextrin (HPBCD) with a degree of substitution (D.S.) of 5 to 7 to result in solutions containing 0, 1, 5 and b 10 weight percent, respectively, or with BHT solution containing 0, 0.1, 0.5, 1, 5 and 10 weight percent, respectively.

Each solution was mixed for three minutes and then sonicated (50% duty cycle, microtip limit output of 10, continuous cycle) for three minutes. The individual solutions were stored in bottles sealed with Teflon ® FEP Film and capped. Each bottle was mechanically rolled during storage to prevent drug settling.

The transdermal patches were prepared as follows. One of the above solutions (50 ml) was poured onto a sheet of SCOTCHPAK ® 1022 release liner containing shims (1"×12"×0.20" thick) placed along the edges (9" apart) and held in place by a tension bar on a coater.

The adhesive solution was drawn down (165 inches/min) at a setting of 5.5 on the motor scale.

The formulations were air-dried for 24 hours to allow the solvent to evaporate.

A sheet of SCOTCHPAK ® 1006 polyester film occlusive backing material was transfer-coated onto the dried formulation, smoothed and laminated with a 4.5 pound rubber roller.

EXAMPLE 5: Effect of BHT Concentration Upon Patch Properties

Transdermal patches were prepared as described in EXAMPLE 4 with BHT used as the permeation enhancer, at concentration of 0, 0.1, 0.5, 1, 5 and 10 weight percent. The performance properties of these patches are shown in TABLE 2, where the rating scale is as described before.

TABLE 2

| Matrix BHT Wt. % | Release | Adhesion | Tack |
|---|---|---|---|
| 0 | 1 | 2 | 3 |
| 10 | 5 | 3 | 1 |
| 5 | 4 | 2 | 1 |
| 1 | 1 | 2 | 2 |

TABLE 2-continued

| Matrix BHT Wt. % | Release | Adhesion | Tack |
|---|---|---|---|
| 0.5 | 2 | 2 | 2 |
| 0.1 | 1 | 2 | 3 |

Patches that contained either 0.1 weight percent, 0.5 weight percent or 1.0 weight percent of BHT exhibited the most desirable properties of easy removal of the release liner, adequate tack and good skin adhesion. At BHT levels above 1 weight percent the properties of the patch are substantially reduced and patches tend to stick together.

EXAMPLE 6: Permeation of DHEA Through Human Skin

Skin samples were obtained from the chest of a 33 year old human female (Skin #1) and the abdomen of a 27 year old human female (Skin #2). The skin samples were placed in separate Franz cells with a contact surface of 5 cm$^2$, and maintained in a solvent of 20% PEG400:80% isotonic aqueous solution at 32+0.5 degrees C.

Circular transdermal patches having an area of about 7.1 cm$^2$ and containing about 30.6 mg DHEA in the presence or absence of either BHT (1% w/w) or HPBCD (5% w/w) were adhered to separate samples, and DHEA permeation measured by HPLC at 24 and 48 hours after application of the patches. Results are shown in TABLE 3 for the rate (flux) and amount of permeation of DHEA. A significant increase in the permeation of DHEA into chest skin (Skin #1) is obtained in the presence of 5% w/w HPBCD, while BHT increased DHEA permeation in abdominal skin (Skin #2) over hours.

TABLE 3

| | Skin #1 | | Skin #2 | |
|---|---|---|---|---|
| | 24 hr | 48 hr | 24 hr | 48 hr |
| Patch Content Flux ($\mu g \cdot cm^{-2} \cdot hr^{-1}$) | | | | |
| DHEA | 0.52 | 0.63 | 1.07 | 1.19 |
| DHEA + BHT | 0.54 | 0.56 | 1.02 | 1.25 |
| DHEA + HPBCD | 0.73 | 0.90 | 0.91 | 1.21 |
| DHEA Concentration in Franz Cell ($\mu g/ml$) | | | | |
| DHEA | 24.66 | 62.34 | 52.50 | 117.32 |
| DHEA + BHT | 22.03 | 54.86 | 50.25 | 123.01 |
| DHEA + HPBCD | 35.98 | 88.13 | 44.64 | 118.96 |
| Total DHEA Permeated (mg) | | | | |
| DHEA | 0.173 | 0.436 | 0.368 | 0.821 |
| DHEA + BHT | 0.154 | 0.384 | 0.352 | 0.861 |
| DHEA + HPBCD | 0.252 | 0.691 | 0.313 | 0.832 |

The foregoing description and the EXAMPLES are intended as illustrative and are not to be taken as limiting. Still other variations within the spirit and scope of this invention are possible and will readily present themselves to those skilled in the art.

I claim:

1. A dosage form for transdermal delivery of dehydroepiandrosterone which comprises an adhesive matrix constituted by a medical-grade pressure-sensitive silicone copolymer adhesive, the dehydroepiandrosterone distributed in said matrix in an amount in the range of about 1 to about 10 percent by weight of the matrix, and a permeation enhancer for said dehydroepiandrosterone present in said matrix in an amount in the range of about 1 to about 10 percent by weight of the matrix; said permeation enhancer being a carbocyclic compound with pendant hydroxyl groups and selected from the group consisting of butylated hydroxytoluene, butylated hydroxyanisole and hydroxypropyl-beta-cyclodextrin, and mixtures thereof.

2. The dosage form of claim 1, wherein said adhesive matrix is composed of a plurality of coextensive matrix layers, each layer containing an amount of dehydroepiandrosterone and permeation enhancer different from that in each matrix layer contiguous thereto.

3. The dosage form of claim 1 further comprising an occlusive backing layer coextensive with said matrix.

4. The dosage form of claim 3, wherein said dosage form is a transdermal patch.

5. The dosage form of claim 4, wherein said permeation enhancer is butylated hydroxyanisole.

6. The dosage form of claim 4, wherein said permeation enhancer is butylated hydroxytoluene.

7. The dosage form of claim 4 wherein said permeation enhancer is a hydroxypropyl-beta-cyclodextrin.

8. The dosage form of claim 7, wherein said hydroxypropyl-beta-cyclodextrin has a degree of substitution of about 5 to about 7.

9. The dosage form of claim 2, wherein each of said coextensive layers contains, independently, a permeation enhancer present in an amount of about 0 to 10 percent by weight of the layer, with the proviso that the total amount of permeation enhancer present in all the layers is in an amount in the range of about 1 to about 10 percent by weight of said adhesive matrix.

10. The dosage form of claim 9, wherein each of said coextensive layers contains, independently, dehydroepiandrosterone in an amount in the range of about 0 to about 10 percent by weight of the layer, with the proviso that the total amount of dehydroepiandrosterone present in all the layers is in an amount in the range of about 1 to about 10 percent by weight of said adhesive matrix.

11. The dosage form of claim 10, wherein contiguous independent layers of said adhesive matrix contain different permeation enhancers.

12. The dosage form of claim 11, wherein said dosage form is a transdermal patch comprising an occlusive backing layer coextensive with an adhesive matrix, said adhesive matrix comprising a first layer contiguous with said occlusive backing layer and comprising DHEA and a hydroxypropyl-beta-cyclodextrin, and a second layer, contiguous with said first layer, comprising DHEA and BHT.

13. The dosage form of claim 11, wherein said dosage form is a transdermal patch comprising an occlusive backing layer coextensive with an adhesive matrix, said adhesive matrix comprising a first layer contiguous with said occlusive backing layer and comprising DHEA and a hydroxypropyl-beta-cyclodextrin, a second layer, contiguous with said first layer comprising DHEA and BHT, and a third layer, contiguous with said second layer, comprising BHT.

* * * * *